United States Patent
Giles et al.

(10) Patent No.: US 10,352,900 B2
(45) Date of Patent: Jul. 16, 2019

(54) FLUSHING ION MOBILITY SEPARATION CELL BETWEEN ION MOBILITY SEPARATION CYCLES

(71) Applicant: Micromass UK Limited, Wilmslow (GB)

(72) Inventors: Kevin Giles, Stockport (GB); Martin Raymond Green, Bowdon (GB); Jason Lee Wildgoose, Stockport (GB)

(73) Assignee: MICROMASS UK LIMITED, Wilmslow (GB)

(*) Notice: Subject to any disclaimer, the term of this patent is extended or adjusted under 35 U.S.C. 154(b) by 0 days.

(21) Appl. No.: 15/118,710

(22) PCT Filed: Feb. 16, 2015

(86) PCT No.: PCT/GB2015/050430
§ 371 (c)(1),
(2) Date: Aug. 12, 2016

(87) PCT Pub. No.: WO2015/121680
PCT Pub. Date: Aug. 20, 2015

(65) Prior Publication Data
US 2017/0059525 A1    Mar. 2, 2017

(30) Foreign Application Priority Data

Feb. 14, 2014  (EP) ..................................... 14155159
Feb. 14, 2014  (GB) ................................... 1402584.5

(51) Int. Cl.
*G01N 27/62* (2006.01)

(52) U.S. Cl.
CPC ................................ *G01N 27/622* (2013.01)

(58) Field of Classification Search
CPC .................................................... G01N 27/622
See application file for complete search history.

(56) References Cited

U.S. PATENT DOCUMENTS

| | | |
|---|---|---|
| 6,674,067 B2 | 1/2004 | Grosshans et al. |
| 6,713,757 B2 | 3/2004 | Tanner et al. |
| 8,188,424 B2 | 5/2012 | Baykut et al. |
| 8,350,212 B2 | 1/2013 | Covey et al. |
| 8,426,802 B2 | 4/2013 | Giles et al. |
| 8,766,170 B2 | 7/2014 | Guna et al. |

(Continued)

FOREIGN PATENT DOCUMENTS

| | | |
|---|---|---|
| GB | 2409764 | 5/2006 |
| GB | 2443952 A | 5/2008 |

OTHER PUBLICATIONS

Martus K E et al., "Theory and Operation of a Three-Gate Time-of-Flight Velocity Analyzer", Review of Scientific Instruments, AIP, Melville, NY, US, vol. 64 No. 2, Feb. 1993.

(Continued)

*Primary Examiner* — David E Smith
*Assistant Examiner* — Sean M Luck
(74) *Attorney, Agent, or Firm* — Womble Bond Dickinson (US) LLP; Deborah M. Vernon; Heath T. Misley

(57) ABSTRACT

An apparatus is provided to separate ions temporally according to a physico-chemical property comprising an ion guide comprising a plurality of electrodes and a first device arranged and adapted to remove undesired ions remaining within the ion guide after ions of interest have exited the ion guide.

20 Claims, 4 Drawing Sheets

(56) References Cited

U.S. PATENT DOCUMENTS

| | | |
|---|---|---|
| 9,293,315 B2 | 3/2016 | Makarov |
| 2008/0164409 A1* | 7/2008 | Schultz ............... G01N 27/622 250/282 |
| 2010/0032561 A1* | 2/2010 | Giles .................. H01J 49/4235 250/283 |
| 2010/0108879 A1 | 5/2010 | Bateman et al. |
| 2013/0298938 A1* | 11/2013 | Bian ................... G01N 27/622 134/1 |

OTHER PUBLICATIONS

Combined Search and Examination Report under Sections 17 and 18(3) dated Mar. 9, 2015 for Application No. GB1502568.7.

* cited by examiner

FLUSHING ION MOBILITY SEPARATION CELL BETWEEN ION MOBILITY SEPARATION CYCLES

CROSS REFERENCE TO RELATED APPLICATIONS

This application is the National Stage of International Application No. PCT/GB2015/050430, filed 16 Feb. 2015 which claims priority from and the benefit of United Kingdom patent application No. 1402584.5 filed on 14 Feb. 2014 and European patent application No. 14155159.8 filed on 14 Feb. 2014. The entire contents of these applications are incorporated herein by reference.

BACKGROUND TO THE PRESENT INVENTION

The present invention relates to an apparatus arranged and adapted to separate ions temporally according to a physico-chemical property such as ion mobility and a method of separating ions temporally according to a physico-chemical property such as ion mobility.

In many analyses involving separation, particularly for a targeted analysis where the mass to charge ratio and/or drift time of analytes of interest is known, the maximum ion mobility drift time of the targeted analyte ions at a given chromatographic retention time is generally known.

In order to improve the duty cycle of an ion mobility separator it is known to accumulate ions in an ion trap upstream of an ion mobility separator prior to releasing the ions into the ion mobility separator and allowing the ions to separate temporally according to their ion mobility. It is advantageous to operate with the fastest ion mobility separation cycle time practical.

Operating at the fastest practical ion mobility separation cycle time reduces the amount of charge which is accumulated in the upstream ion trap prior to ion mobility separation. This limits ion losses or and limits reduction in the performance of the ion mobility separation device due to space charge effects prior to separation.

In addition, relatively fast ion mobility separation cycle times (and hence short accumulation times) advantageously limits the amount of charge for a given analyte within the ion mobility separation device during separation. It is known that space charge effects within ion mobility separation devices can result in distortion of ion mobility separation peak widths and can also result in shifts in measured ion mobility separation drift times.

Furthermore, reducing the number of ions exiting the ion mobility separation device per ion mobility separation cycle reduces the requirement for high dynamic range ion detectors and recording electronics downstream of the ion mobility separation device.

It is therefore advantageous to analyse an ion population eluting from a chromatographic device (such as a liquid chromatography separation device) using a relatively large number of sequential fast ion mobility separation cycles with short accumulation times rather than analysing the ions eluting from the chromatographic device using only a relatively small number of ion mobility separation cycles having longer accumulation times. This maximises the dynamic range over which the entire ion population can be recorded.

However, in many cases, ions from matrix species or other non targeted analyte species which have a relatively low ion mobility and hence will have a longer drift time than the drift time of the analyte ions of interest will still be present in the ion mobility separation device after analyte ions of interest have exited the ion mobility separation device. Accordingly, if a second population of ions is then introduced into the ion mobility separation device before ions which are not of interest and which have relatively low ion mobilities have exited the ion mobility separation device then the ions which are not of interest and which have relatively low ion mobilities will still be present in the ion mobility separation device when the second population of ions is introduced. Accordingly, the undesired ions having relatively low ion mobilities will undesirably appear in the second ion mobility separation cycle and will appear to have relatively short ion mobility separation drift times. Accordingly, the undesired ions which remain in the ion mobility separation device after analyte ions of interest have exited the ion mobility separation device will cause aliasing or wrap around effects. The resulting aliasing or wrap around effects may result in interferences and/or misassignment of ion mobility or calculated collision cross section ("CCS") values.

The problem of aliasing or wrap around effects is a particularly serious problem in a High Definition $MS^e$ ("$HDMS^e$") type experiment wherein fragment ions resulting from fragmenting parent or precursor ions which emerge from an ion mobility separation device may interfere in mass to charge ratio and ion mobility.

US 2010/0032561 (Micromass) discloses an ion tunnel device which may be operated in a first mode wherein ions are separated temporally according to their ion mobility and in a second mode wherein ions are separated temporally according to their mass to charge ratio.

US 2010/108879 (Micromass) discloses a mass spectrometer comprising an ion mobility separation device. In one arrangement, once ions with a desired charge state have exited the ion mobility separation device, the AC or RF voltage applied to the ion mobility separation device may be removed so that any undesired ions still in the device are no longer radially confined and hence are allowed to disperse.

WO 02/071439 (Tanner) discloses a mass spectrometer comprising a processing section such as a collision cell. An axial field and a DC voltage flush pulse may be applied to the collision cell in order to affect the charge distribution within the collision cell.

It is desired to provide an improved mass spectrometer and an improved method of mass spectrometry.

SUMMARY OF THE PRESENT INVENTION

According to an aspect of the present invention there is provided apparatus arranged and adapted to separate ions temporally according to their ion mobility or differential ion mobility comprising:

an ion guide comprising a plurality of electrodes; and a first device arranged and adapted to remove undesired ions remaining within the ion guide after ions of interest have exited the ion guide;

wherein the apparatus comprises a control system which is arranged and adapted:

(i) to cause the apparatus to operate in a first mode of operation wherein ions are separated temporally according to a their ion mobility or differential ion mobility during a first time period T1; and then (ii) to switch the apparatus to operate in a second mode of operation wherein undesired ions are substantially ejected, flushed out or otherwise removed from the ion guide during a second time period T2;

wherein the control system is further arranged and adapted to apply either one or more first transient DC voltages or potentials to the electrodes having a first amplitude and/or a first transient velocity or one or more first DC voltages or potentials to the electrodes so as to produce a first DC voltage or potential gradient within or along the ion guide during the first mode of operation so as to cause ions to separate temporally within the ion guide according to their ion mobility or differential ion mobility during the first mode of operation; and wherein the control system is further arranged and adapted to apply either one or more second transient DC voltages or potentials to the electrodes having a second amplitude and/or a second transient velocity or one or more second DC voltages or potentials to the electrodes so as to produce a second DC voltage or potential gradient within or along the ion guide during the second mode of operation so as to cause ions to be ejected from the ion guide during the second mode of operation.

The present invention solves the problem of aliasing of ion mobility separation peaks and allows the ion mobility separation cycle time to be optimised for a given experiment.

In order to prevent unwanted aliasing effects the ion mobility separation device or cell is, according to the preferred embodiment, preferably flushed of remaining undesired ions once ions of interest have eluted from the ion mobility separation device or cell. Unwanted or undesired ions which remain or which are otherwise still present within the ion mobility separation device or cell are preferably flushed or otherwise ejected from the ion mobility separation device or cell before a next or subsequent pulse of ions is preferably introduced into the ion mobility separation device. Ions which are desired to be subsequently temporally separated in the ion mobility separation device are preferably accumulated in an upstream accumulation device or ion trap during the flushing time or time period during which time undesired ions are preferably being ejected from the ion mobility separation device or cell.

The preferred embodiment advantageously allows ion mobility separation analysis of analyte ions to be performed within any defined ion mobility range without suffering from interference or aliasing effects resulting from ions having relatively low ion mobilities.

As the maximum ion mobility separation drift time required for an analysis preferably changes during elution of analytes from an upstream chromatographic separation device (such as a liquid chromatography device) the duration of the ion mobility separation cycle preferably changes during the analysis in order to maintain the optimum ion mobility separation cycle time based upon the various different target compounds of interest present in the sample being analysed.

It is known to flush a collision gas cell of ions during an inter-scan period in order to minimise cross talk between different populations of ions when the state of the instrument is changed. However, gas cells are not separation devices and known arrangements do not progressively adjust the time at which flushing of undesired ions occurs based upon particular analyte ions.

In this regard, it will be appreciated that the present invention is distinct from the arrangement described in WO 02/071439 (Tanner) wherein a DC voltage flush pulse may be used to remove ions from a collision cell (which is not a separation device). By contrast, the present invention is concerned with removing undesired ions from an ion guide in a second mode of operation, wherein in a previous first mode of operation ions are separated temporally within or along the ion guide according to their ion mobility or differential ion mobility.

The control system of the present invention is arranged and adapted to apply one or more DC voltages or potentials to the electrodes of the ion guide so as to cause ions to separate temporally within the ion guide according to their ion mobility or differential ion mobility during a first mode of operation. According to a particularly preferred embodiment, the one or more DC voltages or potentials applied to the electrodes during the first mode of operation comprise DC transient voltages or potentials having a first amplitude and preferably a first transient velocity or first switching time. In less preferred embodiments, the one or more DC voltages or potentials applied to the electrodes during the first mode of operation may comprise one or more DC voltages or potentials that produce a first DC voltage or potential gradient within or along the ion guide.

The control system of the present invention is further arranged and adapted to apply one or more DC voltages or potentials to the electrodes of the ion guide so as to cause ions to be ejected from the ion guide during a second mode of operation. According to a particularly preferred embodiment, the one or more DC voltages or potentials applied to the electrodes during the second mode of operation comprise transient DC voltages or potentials having a second amplitude and preferably a second transient velocity or second switching time. In less preferred embodiments, the one or more DC voltages or potentials applied to the electrodes during the second mode of operation comprise one or more DC voltages or potentials that produce a second DC voltage or potential gradient within or along the ion guide.

Therefore, the present invention actively ejects ions from the ion guide during the second mode of operation by applying DC voltages or potentials to the electrodes of the ion guide. Actively ejecting the ions in this manner is particularly advantageous since it allows these unwanted ions to be removed from the ion guide over a shorter time period compared to other methods. Thus the present invention is distinct from the method of US 2010/108879 (Micromass), for example, which does not disclose applying DC voltages to the electrodes of the ion guide in order to eject ions, but which instead allows ions to radially disperse from the ion guide over a longer time period by switching OFF the radially confining RF electric fields.

The apparatus preferably further comprises a second device which is arranged and adapted to pulse ions into the ion guide.

The second device preferably comprises an ion trap or ion gate.

The second device is preferably arranged and adapted to pulse a first group of ions into the ion guide and the first device is arranged and adapted to remove the undesired ions from the ion guide prior to the introduction of a second or subsequent pulse of ions into the ion guide.

According to a less preferred embodiment a portion at the front of the ion guide may substantially never be emptied of ions during use. According to this less preferred embodiment undesired ions are arranged to pass into a second section of the ion guide after the time when ions of interest have eluted. The second section of the ion guide may then be cleared or removed of ions at substantially the same time as a second pulse of ions is introduced into the front of the ion guide. According to this less preferred embodiment the flush pulse is preferably over before ions having the highest ion mobility reach the second part of the ion guide.

The control system is preferably arranged and adapted to set the first time period T1 and the second time period T2 so that T2<T1.

The control system is preferably arranged and adapted to repeatedly switch between at least the first mode of operation and the second mode of operation multiple times during the course of a single acquisition.

The control system is preferably arranged and adapted to progressively vary, decrease or increase the first time period T1 during the course of an acquisition.

The control system may be arranged and adapted to progressively vary, decrease or increase the second time period T2 during the course of an acquisition.

The control system is preferably arranged and adapted to maintain the second time period T2 substantially constant during the course of an acquisition.

The first amplitude is preferably selected from the group consisting of: (i) <5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V.

The control system may be arranged and adapted to maintain the first amplitude substantially constant during the first mode of operation.

The control system is preferably arranged and adapted to vary, decrease or increase the first amplitude during the first mode of operation.

The control system is preferably arranged and adapted to apply the one or more first transient DC voltages or potentials to the electrodes at a first rate or first velocity during the first mode of operation so as to cause ions to separate temporally within the ion guide according to their ion mobility or differential ion mobility during the first mode of operation.

The first rate or first velocity is preferably selected from the group consisting of: (i) <50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s.

The control system is preferably arranged and adapted to maintain the first rate or first velocity substantially constant during the first mode of operation.

The control system may be arranged and adapted to vary, increase or decrease the first rate or first velocity during the first mode of operation.

According to an embodiment in the first mode of operation the ion guide is maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

The second amplitude is preferably selected from the group consisting of: (i) <5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V.

The second amplitude is preferably greater than (or less than or the same as) the first amplitude.

The second DC voltage or potential gradient is preferably of greater (or lesser or equal) magnitude than the first DC voltage or potential gradient.

The control system is preferably arranged and adapted to apply the one or more second transient DC voltages to the electrodes at a second rate or second velocity during the second mode of operation so as to cause ions to be ejected from the ion guide during the second mode of operation.

The second rate or second velocity is preferably selected from the group consisting of: (i) <50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s.

The second rate or second velocity is preferably less than (or greater than or the same as) the first rate or first velocity.

According to an embodiment in the second mode of operation the ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to another aspect of the present invention there is provided a mass spectrometer comprising apparatus as described above.

According to an aspect of the present invention there is provided a method of separating ions temporally according to their ion mobility or differential ion mobility comprising:

providing an ion guide comprising a plurality of electrodes; and removing undesired ions remaining within said ion guide after ions of interest have exited said ion guide;

the method further comprising:

applying either one or more first transient DC voltages or potentials to said electrodes having a first amplitude and/or a first transient velocity or one or more first DC voltages or potentials to said electrodes so as to produce a first DC voltage or potential gradient within or along said ion guide during said first mode of operation so as to cause ions to separate temporally within said ion guide according to their ion mobility or differential ion mobility during a first time period T1 in a first mode of operation; and then applying either one or more second transient DC voltages or potentials to said electrodes having a second amplitude and/or a second transient velocity or one or more second DC voltages or potentials to said electrodes so as to produce a second DC voltage or potential gradient within or along said ion guide during said second mode of operation so as to cause ions to be ejected from said ion guide during a second time period T2 in a second mode of operation.

The method preferably further comprises pulsing ions into the ion guide.

The method preferably further comprises using an ion trap or ion gate to pulse ions into the ion guide.

The method preferably further comprises pulsing a first group of ions into the ion guide and removing undesired ions from the ion guide prior to the introduction of a second or subsequent pulse of ions into the ion guide.

The method preferably further comprises setting the first time period T1 and the second time period T2 so that T2<T1.

The method preferably further comprises repeatedly switching between at least the first mode of operation and the second mode of operation multiple times during the course of a single acquisition.

The method preferably further comprises progressively varying, decreasing or increasing the first time period T1 during the course of an acquisition.

The method preferably further comprises progressively varying, decreasing or increasing the second time period T2 during the course of an acquisition.

The method preferably further comprises maintaining the second time period T2 substantially constant during the course of an acquisition.

The first amplitude is preferably selected from the group consisting of: (i) <5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V.

The method preferably further comprises maintaining the first amplitude substantially constant during the first mode of operation.

The method may further comprise varying, decreasing or increasing the first amplitude during the first mode of operation.

The method preferably further comprises applying the one or more first transient DC voltages or potentials to the electrodes at a first rate or first velocity during the first mode of operation so as to cause ions to separate temporally within the ion guide according to their ion mobility or differential ion mobility during the first mode of operation.

The first rate or first velocity is preferably selected from the group consisting of: (i) <50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s.

The method preferably further comprises maintaining the first rate or first velocity substantially constant during the first mode of operation.

The method preferably further comprises varying, increasing or decreasing the first rate or first velocity during the first mode of operation.

In the first mode of operation the ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

The second amplitude is preferably selected from the group consisting of: (i) <5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V.

The second amplitude is preferably greater than the first amplitude.

The second DC voltage or potential gradient is preferably of greater magnitude than the first DC voltage or potential gradient.

The one or more second transient DC voltages or potentials are preferably applied to the electrodes at a second rate or second velocity during the second mode of operation so as to cause ions to be ejected from the ion guide during the second mode of operation.

The second rate or second velocity is preferably selected from the group consisting of: (i) <50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s.

The second rate or second velocity is preferably less than the first rate or first velocity.

In the second mode of operation the ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to another aspect of the present invention there is provided a method of mass spectrometry comprising a method as described above.

According to an aspect of the present invention there is provided apparatus arranged and adapted to separate ions temporally according to a physico-chemical property comprising:

an ion guide comprising a plurality of electrodes; and a first device arranged and adapted to remove undesired ions remaining within the ion guide after ions of interest have exited the ion guide.

According to a less preferred embodiment the physico-chemical property comprises mass or mass to charge ratio.

The first device is preferably arranged and adapted to remove undesired ions remaining within the ion guide after ions of interest have exited the ion guide by changing, increasing or reducing the amplitude and/or frequency and/or phase of one or more AC or RF potentials applied to the plurality of electrodes.

The first device is preferably arranged and adapted to remove undesired ions remaining within the ion guide after ions of interest have exited the ion guide by applying one or more deflection voltages across one or more portions of the ion guide.

The first device is preferably arranged and adapted to remove undesired ions remaining within the ion guide after ions of interest have exited the ion guide by applying one or more pulses of gas or other substances to the ion guide.

According to another aspect of the present invention there is provided a mass spectrometer comprising apparatus as described above.

According to another aspect of the present invention there is provided a method of separating ions temporally according to a physico-chemical property comprising:

providing an ion guide comprising a plurality of electrodes; and removing undesired ions remaining within the ion guide after ions of interest have exited the ion guide.

According to another aspect of the present invention there is provided a method of mass spectrometry comprising a method as described above.

According to an aspect of the present invention there is provided a method of mass spectrometry comprising:

introducing a population of ions into an ion mobility separation or mass to charge ratio separator device;

separating the ions according to their ion mobility and/or mass to charge ratio for a period of time T1 after which ions of interest have exited said device;

removing, preferably in a rapid manner, any ions still within the device after a time period T1 during a subsequent time period T2 wherein T2<T1; and introducing a second population of ions into the device.

The time period T1 may vary with time.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector preferably selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD"). Additionally or alternatively, the chromatography detector may comprise a non-destructive chromatography detector preferably selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment, analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenylanthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

A preferred embodiment of the present invention will now be described with reference to FIG. 1A.

Figure 1A:
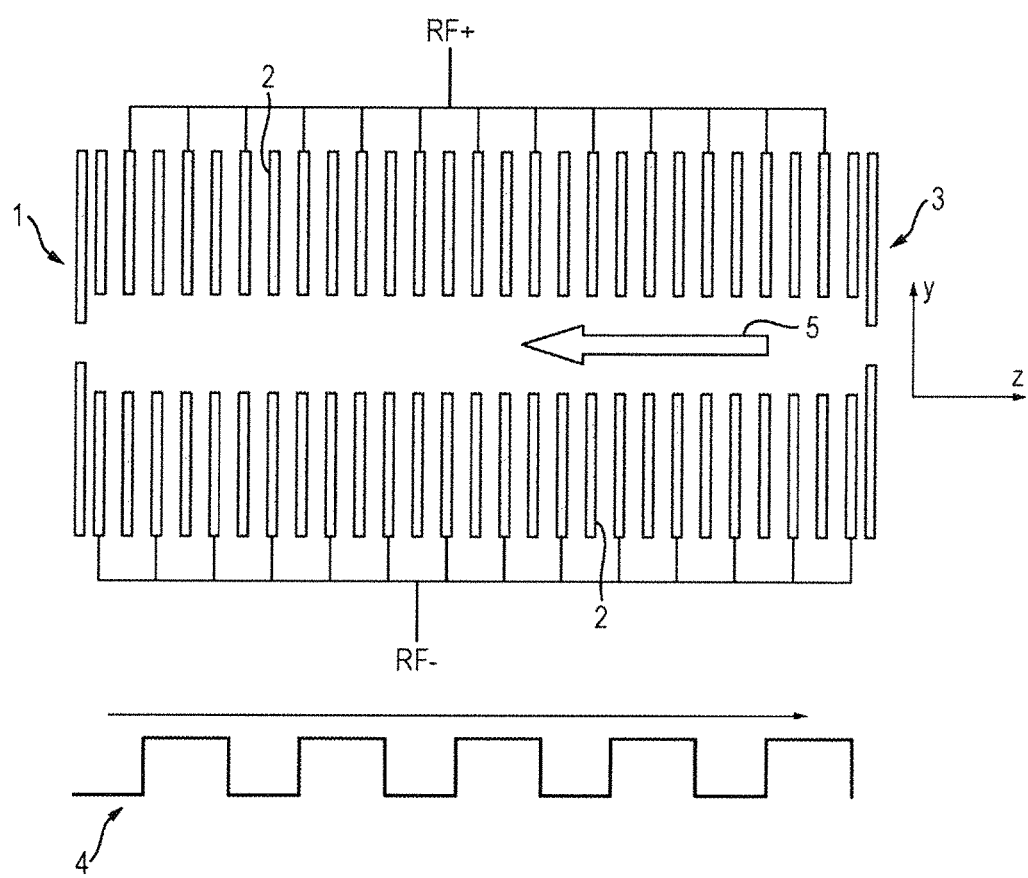
FIG. 1A shows an ion mobility separation device which is preferably utilised according to a preferred embodiment of the present invention in the (y,z) dimension

FIG. 1A shows an ion mobility separation device according to a preferred embodiment of the present invention wherein the ion mobility separation device comprises a plurality of electrodes which preferably comprise an RF confined ring stack. The ion mobility separation device preferably comprises an entrance electrode 1, a series of ring electrodes 2 and an exit electrode 3. Opposite phases of an AC voltage or potential which preferably oscillates at RF frequency are preferably applied to alternate ring electrodes 2 in order to produce a radial RF confining force such that ions within the ion mobility separation device are preferably radially confined within the ion mobility separation device by a radial pseudo-potential barrier.

Figure 1B:
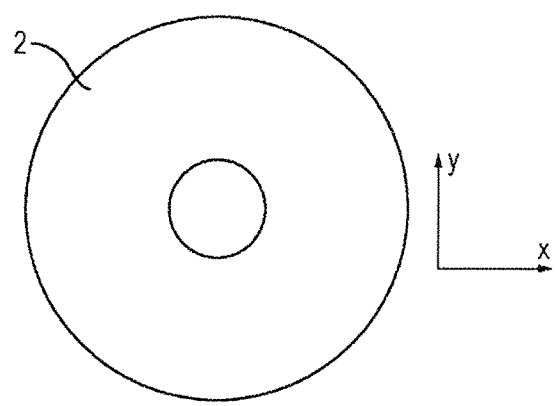
FIG. 1B shows a ring electrode of the ion mobility separation device in the (x,y) dimension.

FIG. 1A shows the ion mobility separation device in the (y,z) dimension and FIG. 1B shows an individual ring electrode 2 of the ion mobility separation device in the (x,y) dimension. In operation ions are preferably pulsed into the ion mobility separation device and once the ions have entered the ion mobility separation device the ions are then preferably urged from the entrance 1 of the ion mobility separation device towards the exit 3 of the ion mobility separation device by the application of one or more travelling DC voltage waves or potentials 4 which are preferably applied to the electrodes comprising the ion mobility separation device. The one or more DC voltage or potential waves preferably comprise one or more transient DC voltages or potentials which are preferably applied to the ring electrodes 2 at a first transient velocity and which preferably urge ions from the entrance 1 to the exit 3 of the ion mobility separation device.

Figure 2A:
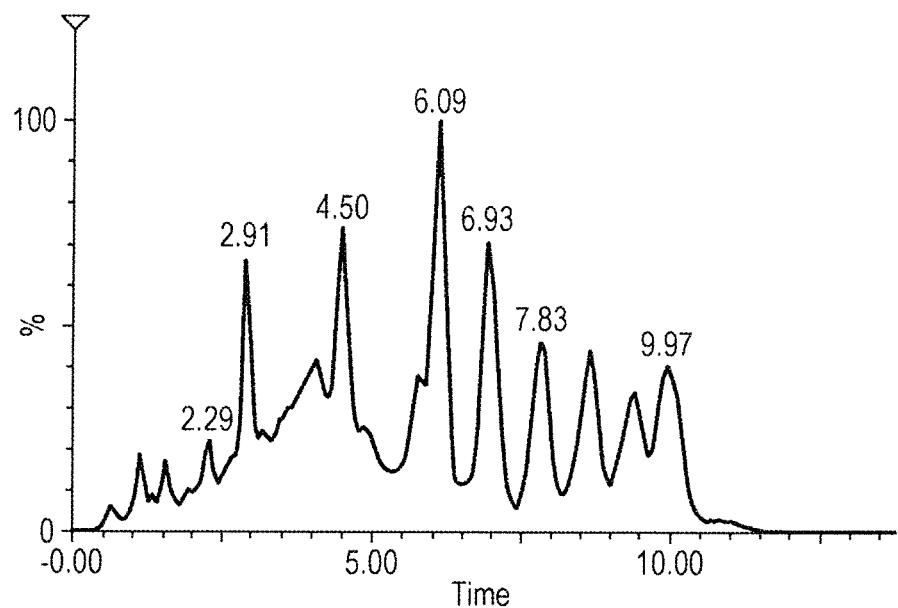
FIG. 2A shows an ion mobility separation spectrum reltaing to the various different fragment ions resulting from fragmenting doubly charged Glu Fibrinopeptide $[M+H]^{2+}$ parent ions having a mass to charge ratio 785.6 in a Collision Induced Dissociation ("CID") cell and then temporally separating the resulting fragment ions in a preferred ion mobility separation device
Figure 3:
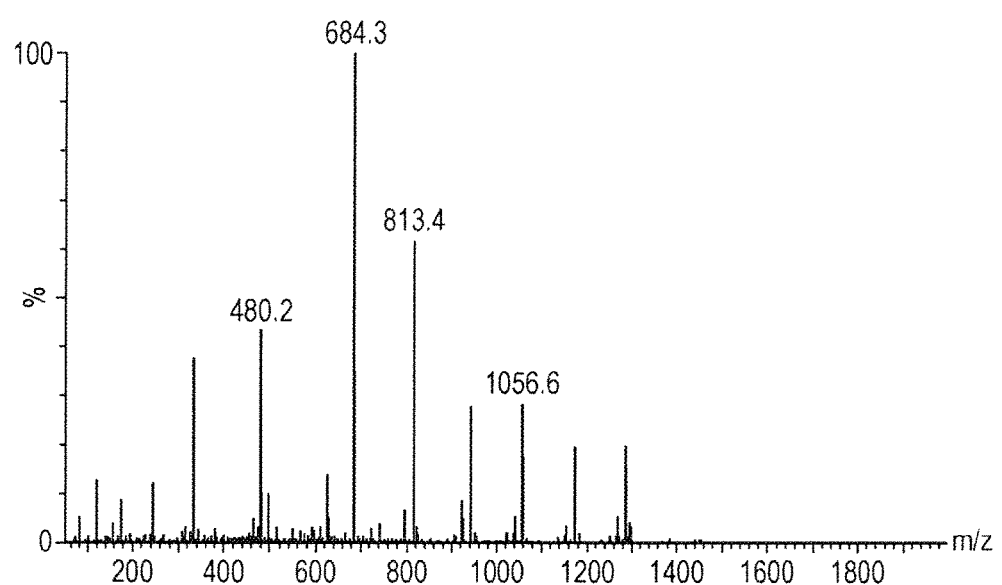
FIG. 3 shows a fragment ion mass spectrum relating to the fragment ions resulting from CID fragmentation of Glu Fibrinopeptide $[M+H]^{2+}$ parent ions having a mass to charge ratio 785.6.

FIG. 2A shows an ion mobility separation spectrum of fragment ions resulting from fragmenting doubly charged Glu Fibrinopeptide $[M+H]^{2+}$ parent ions having a mass to charge ratio of 785.6 in a Collision Induced Dissociation ("CID") fragmentation device and then passing the resulting fragment ions into the ion mobility separation device in order to temporally separate the fragment ions. A corresponding mass spectrum of the fragment ions is shown in FIG. 3.

The ion mobility separation spectrum as shown in FIG. 2A was obtaining by setting the travelling wave velocity (i.e. the first transient velocity or the effective speed or rate at which the one or more transient DC voltages or potentials were progressively applied to the ring electrodes 2 along the axial length of the ion mobility separation device) to 650 m/s and also ramping the amplitude of the travelling wave (i.e. the amplitude of the one or more first transient DC voltages or potentials which were applied to the electrodes 2) from 22.2 V to 40 V during the course of the ion mobility separation time.

The ion mobility separation device was maintained at approximately 2.5 mbar of nitrogen and the length of the ion mobility separation device was 250 mm. Under these conditions ions preferably travel along and through the ion mobility separation device with a velocity which is preferably related to their ion mobility i.e. ions are preferably temporally separated according to their ion mobility.

The longest drift time for the lowest mobility product ions was approximately 10 ms. Ions which are temporally separated within the preferred ion mobility separation device preferably travel or otherwise pass along the axial length of the ion mobility separation device with a velocity which is significantly slower than the velocity of the travelling DC potential or voltage wave i.e. the ions may progress along the length of the ion mobility separation device at a velocity of, for example, approximately 25 m/s whereas the transient DC voltages or potentials may effectively be applied to or translated along the electrodes 2 at a significantly greater rate or velocity of, for example, 650 m/s. Accordingly, ions effectively roll over the DC voltage wave fronts many times during the course of the ion mobility separation. This effect is fundamental to obtaining ion mobility separation.

In order to illustrate the utility of the present invention a target ion of interest may be considered which is pulsed into the above described ion mobility separation device together with other ions which are not of interest. The target ion of interest may elute from the ion mobility separation device just before 3 ms. In this case all ions exiting the cell after 3 ms are not of interest.

If the ion mobility separation cycle time i.e. the time between subsequent releases of packets of ions or pulses of ions into the ion mobility separation device was decreased to encompass only this drift time range then ions which would be expected to elute after 3 ms would still be within the ion mobility separation device during the next ion mobility separation. As a result, these ions would appear in the subsequent ion mobility separation spectrum at an apparently earlier drift time. It is apparent, therefore, that the ion mobility separation device would suffer from aliasing or wrapping around effects.

Aliasing or wrapping around effects would cause potentially significant problems. The potential aliasing or wrapping around effects will now be described in more detail with reference to FIGS. 4A and 4B.

Figure 4A:
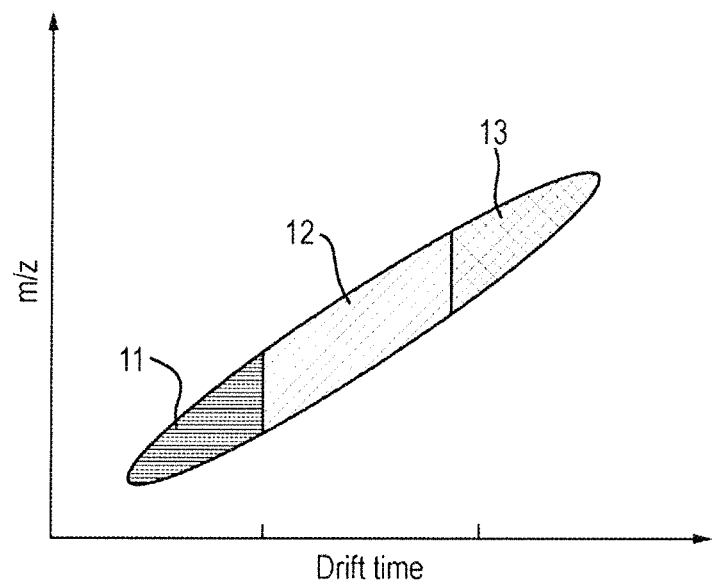
FIG. 4A shows a two dimensional nested IMS-MS data set and FIG. 4B illustrates the problem of aliasing or wrap around by showing the same data as shown FIG. 4A but wherein the ion mobility separation drift time has been shortened and subsequent packets of ions are pulsed into the ion mobility separation device whilst other ions are still present within the ion mobility separation device.

FIG. 4A shows a two dimensional nested IMS-MS data set showing the relationship between the ion mobility drift time of a group of ions and their mass to charge ratio. The area within the ellipse shown in FIG. 4A represents the IMS-MS space occupied by singly charged ions having different mass to charge values such as the fragment ions which might be generated by fragmenting Glu Fibrinopeptide $[M+H]^{2+}$ parent ions having a mass to charge ratio 785.6 in a Collision Induced Dissociation ("CID") cell as detailed above in relation to FIGS. 2A and 3.

In normal operation several nested IMS-MS data sets may be summed in order to produce a summed two dimensional nested IMS-MS plot such as is shown in FIG. 4A.

Figure 4B:
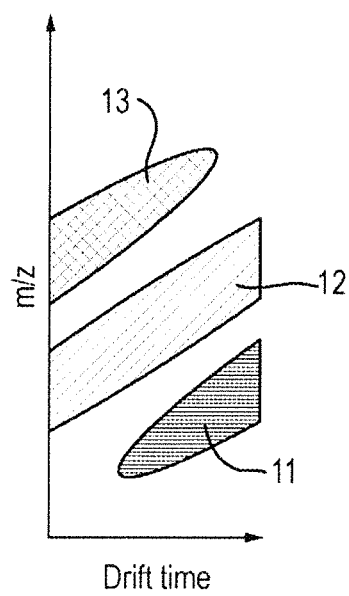

FIG. 4B shows the same ions as shown in FIG. 4A except that the maximum ion mobility drift time before releasing a subsequent packet of ions into the ion mobility separation device has now been reduced. The drift time for each species is calculated relative to the injection of ions into the ion mobility separation device ($T_0$).

It is apparent that if the ion mobility cycle time were reduced in the manner as shown in FIG. 4B then ions 11 having relatively high ion mobilities and hence relatively low drift times would emerge from the ion mobility separation device during the first cycle. During a second cycle when a new pulse of ions is admitted into the ion mobility separation device ions 12 having intermediate ion mobilities and hence intermediate drift times would still be present within the ion mobility separation device from the first cycle and would emerge during the course of the second cycle. During a third cycle when a further pulse of ions is admitted into the ion mobility separation device ions 13 having relatively low ion mobilities and hence relative long drift times would still be present within the ion mobility separation device from the first cycle and would hence would emerge during the course of the third cycle.

In summary, as illustrated by FIG. 4B, ions having a relatively low ion mobility (and hence a long drift time) and a relatively high mass to charge ratio will not have exited an ion mobility separation device before a subsequent pulse of ions is released into the ion mobility separation device. Accordingly, ions having a relatively low ion mobility and a relatively high mass to charge ratio will appear at low drift times in subsequent ion mobility separation spectra.

As will be appreciated, this effect is particularly problematic if the ions which emerge from the ion mobility separation device are then subjected to fragmentation so as to produce a plurality of product or fragment ions since the probability of interference and misassignment of fragment ions to corresponding parent or precursor ions is significantly increased.

The preferred embodiment seeks to substantially prevent any aliasing or wrapping around effects which are highly undesirable by sweeping or flushing ions which remain in the ion mobility separation cell after the desired separation time and prior to a subsequent packet of ions being introduced or pulsed into the ion mobility separation device.

According to an embodiment of the present invention ions may be swept or flushed from the ion mobility separation device after a desired ion mobility separation time by adjusting a travelling wave parameter or one or more parameters of one or more (second) transient DC voltages or potentials which are preferably applied to the electrodes 2. For example, if one or more transient DC voltages or potentials are applied to the electrodes 2 comprising the ion mobility separation device so that the transient DC voltages or potentials are effectively translated along the length of the ion mobility separator at a relatively high velocity then ions will preferably roll over the DC potentials as the transient DC voltages or potentials are translated along the length of the ion mobility separator and hence ions will be separated temporally according to their ion mobility. If, however, the effective velocity or rate at which the one or more (second) transient DC voltages or potentials are translated along the length of the ion mobility separator is slowed down then it can be arranged such that ions within the ion mobility separator will substantially all be driven or urged along and through the length of the ion mobility separation cell at or near the velocity of the (second) DC travelling wave i.e. at the velocity at which the one or more transient DC voltages or potentials are effectively translated along the axial length of the ion mobility separation device.

Figure 2B:
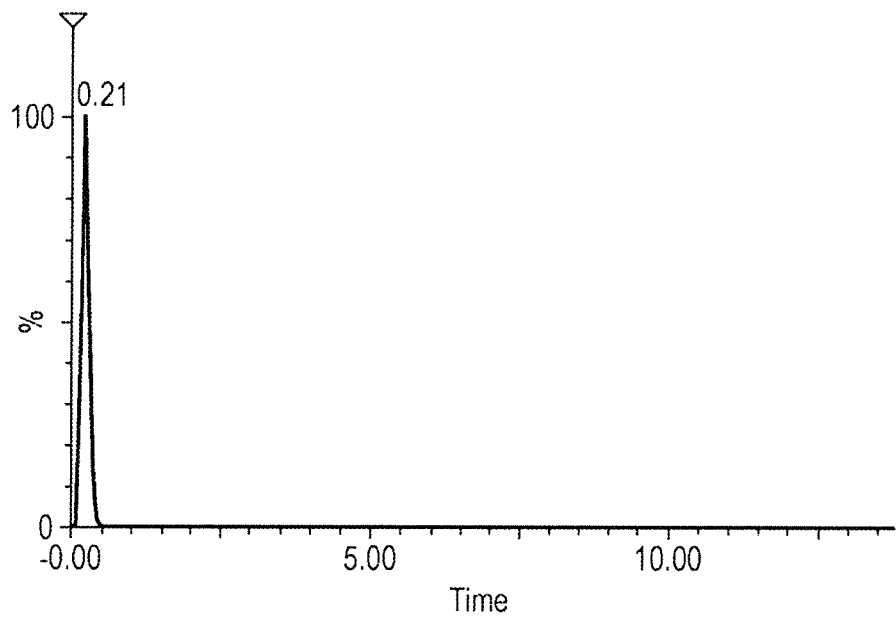
FIG. 2B illustrates a preferred aspect of the present invention wherein in a mode of operation ions are substantially flushed out from the preferred ion mobility separation device in a relatively short period of time.

FIG. 2B shows data relating to the same fragment ions as shown in FIG. 2A but illustrates a preferred embodiment of the present invention wherein all the fragment ions were flushed from the ion mobility separation device in <0.5 ms rather than being allowed to separate temporally and emerge from the ion mobility separation device over a time period of 10 ms. The ions are preferably flushed from the ion mobility separation device according to a preferred embodiment of the present invention by applying a (second) travelling DC wave or one or more (second) transient DC voltages or potentials to the electrodes 2 comprising the ion mobility separation device and setting the height or amplitude of the (second) DC travelling wave or the amplitude of the one or more (second) transient DC voltages or potentials to be 40 V.

Furthermore, the one or more (second) transient DC voltages or potentials were effectively applied to the electrodes 2 in a manner such that the one or more (second) transient DC voltages or potentials were effectively translated along the length of the ion mobility separation device with a reduced effective velocity of 220 m/s. It will be apparent that the velocity at which the one or more (second) transient DC voltages or potentials are effectively translated along the length of the ion mobility separator is less than the velocity at which the one or more (first) transient DC voltages or potentials are effectively translated along the length of the ion mobility separator in order to cause ions to separate temporally according to their ion mobility.

As is apparent from FIG. 2B, when the ion mobility separation device is operated in a mode of operation wherein ions are desired to be flushed out from the ion mobility separation device then the ions can be driven out of the ion mobility separation device or cell in around 0.4 ms. According to the preferred embodiment in order to flush all ions out of the ion mobility separation device at substantially the same time, the (second) transient DC potentials or voltages which are applied to the electrodes 2 comprising the ion mobility separation device are preferably translated along the length of the ion mobility separation device at a substantially lower wave velocity. As a result, according to the preferred embodiment in the mode of operation when ions are desired to be flushed out of the ion mobility separation device preferably all the ions are travelling at or close to the velocity of the (second) travelling wave i.e. the effective speed or velocity at which the transient DC voltages or potentials are applied to the electrodes 2 along the length of the ion mobility separation device. According to the preferred embodiment when flushing ions out of the ion mobility separation device the transient DC voltages are applied with an amplitude and at a velocity (or second switching time) such that there is very little or effectively no roll over of ions occurring and hence as a result there is little or no ion mobility separation.

With respect to the example described, a packet of ions may be released into the ion mobility separation device or cell and the ions are preferably allowed to separate temporally under the same conditions described above in relation to the results shown in FIG. 2A for 3 ms in order to ensure that the target ions of interest have eluted. According to the preferred embodiment after 3 ms the travelling wave parameters are then preferably changed to the conditions as described above in relation to the mode of operation for flushing out ions from the ion mobility separation device as described above in relation to FIG. 2B. As a result, any ions remaining within the ion mobility separation device are preferably driven out of the ion mobility separation device or cell within a time period of approximately 0.4 ms.

During the flushing time wherein remaining ions are effectively ejected from the ion mobility separation device in a rapid manner it is desirable, although not essential, to cease from acquiring ion mobility separation data to disk. It is also generally desirable but not essential to continue accumulation of ions in a pre-ion mobility separation accumulation device or ion trap during the flushing time wherein the ion trap is preferably arranged upstream of the ion mobility separation device.

After 0.4 ms when all ions have effectively been flushed out or otherwise ejected from the ion mobility separation device the next packet of ions is preferably released into the ion mobility separation device. This process may be repeated until a different maximum drift time is required.

In the example given above the overall cycle time of the ion mobility separation required in order to eliminate aliasing is advantageously decreased from approximately 10 ms to approximately 3.4 ms. The pre-ion mobility separation accumulation device or ion trap may continue filling with ions during the flushing process thereby maintaining a 100% duty cycle for the target ions without loss of duty cycle and hence sensitivity. This increases the dynamic range of the overall experiment and decreases any space charge by a factor of ×3.

It should be noted that the ion mobility separation conditions need not be changed when the ion mobility separation cycle time is reduced in order to accommodate the maximum drift time of the target species. Accordingly, the ion mobility separation calibration parameters are preferably not changed and collision cross section may be calculated without recalibration as the ion mobility separation cycle is adjusted. In addition, the total pre-ion mobility separation accumulation time is reduced to a minimum value. This has the effect of minimising space charge distortion effects in the pre-ion mobility separation accumulation device or ion trap and within the ion mobility separation device itself.

It is possible, by drastically changing the ion mobility separation conditions, for example, and/or by altering the travelling wave height or amplitude and/or the effective velocity of the DC travelling wave and/or the buffer gas pressure so as to arrange for all the ions across the total mobility range to elute within 3 ms. However, this would not only change the calibration parameters but would also lead to poor or substantially non optimised ion mobility separation resolution or separation power of the targeted analyte. In any event it should be noted that this would be very difficult to achieve using an ion mobility separation incorporating a static DC field. To increase the transit time sufficiently the potential would need to be impractically high.

The preceding description relates to a preferred embodiment of the present invention, wherein transient DC voltages are applied to the electrodes of the ion guide so as to cause ions to separate temporally within the ion guide according to their ion mobility or differential ion mobility. In less preferred embodiments, however, ions may be separated temporally within the ion guide according to their ion mobility or differential ion mobility using a DC voltage gradient produced within the ion guide that is formed by applying potentials to the electrodes of the ion guide. This DC voltage gradient may be a static DC voltage gradient, for example.

Similarly, in the most preferred embodiment described above, transient DC voltages are applied to the electrodes of the ion guide so as to cause ions to be ejected from the ion guide. In less preferred embodiments, however, ions may be ejected from the ion guide using a DC voltage gradient produced within the ion guide that is formed by applying potentials to the electrodes of the ion guide. This DC voltage gradient may be a static DC voltage gradient, for example.

Thus the present invention provides for separating ions according to their ion mobility or differential ion mobility using DC potential waves or using a DC potential gradient, and further provides for flushing ions from the ion mobility separation device using travelling DC voltage waves or using a DC potential gradient.

In embodiments wherein a first DC voltage gradient is used to separate the ions, and a second DC voltage gradient is used to flush the ions, the second DC voltage gradient is preferably larger in magnitude than the first DC voltage gradient.

Several different methods of flushing ions from an ion mobility separation device or cell according to various embodiments of the present invention may be utilised.

For example, according to an embodiment the RF amplitude of the RF voltage applied to the electrodes 2 forming the ion mobility separation device may be reduced in order to reduce the radial trapping efficiency. As a result, the travelling wave potential applied to the electrodes 2 will result in some ions being pushed out of the ion mobility separation device or cell radially or in a substantially radial direction. As a result, ions either exit the ion mobility separation device or cell radially and hence are lost to the system or else the ions may hit a side edge of one of ring electrodes 2 and hence be annihilated.

According to an embodiment of the present invention the ion tunnel or ion mobility separation device may be split lengthwise allowing a deflection voltage to be applied across all or a portion of the ion mobility separation device or cell. This may be used in conjunction with reduced trapping efficiency by lowering the RF amplitude. This embodiment preferably allows ions to be removed from a specific location or location within the device. According to a less preferred embodiment the ion guide may be split into two regions. In a first portion of the ion guide, near to the entrance of the device, no flushing pulse is preferably applied after ions of interest have exited the device. In a second portion near to the exit of the device a flushing pulse is preferably applied when ions of interest have exited the device. Depending on the range of mobilities within the sample population this embodiment allows a second packet of ions to be introduced into the first portion of the device during the time unwanted ions are flushed out of the second portion of the device thereby increasing the duty cycle.

According to another embodiment a controlled pulse of gas may be used to flush or assist in flushing the ion mobility separation device or cell of unwanted ions. This method is particularly applicable to atmospheric pressure ion mobility separation devices or cells.

Various further embodiments are also contemplated wherein a combination of the above described methods of flushing ions from the ion mobility separation device or cell may be used in order to speed up further the flush time or time taken to eject unwanted ions from the ion mobility separation device.

The approach of flushing a device of unwanted ions according to an embodiment of the present invention may also be applied to other devices other than devices wherein ions are separated temporally according to their ion mobility. For example, according to an embodiment of the present invention the preferred method of flushing the device may also be applied to a travelling wave mass separator such as is described in US 2010/0032561 (Micromass), the contents of which are incorporated herein by reference, wherein in a mode of operation ions are separated temporally according to their mass to charge ratio rather than according to their ion mobility.

Further embodiments are contemplated wherein a similar effect can be achieved by using a non-linear or segmented travelling wave amplitude and/or velocity ramp rather than utilising an abrupt change from optimum ion mobility separation conditions to maximum flush out conditions. The abrupt change from separating to flushing is, however, preferred as it allows optimisation of the ion mobility separation separation conditions and minimises flush out time but it is not essential that the conditions be abruptly altered.

The ion mobility separation conditions may be changed to optimise the separation conditions for each target analyte and preferably this change should then be taken into account if collision cross section ("CCS") information is required. The various modes of flushing ions from the preferred device as described above may be used in conjunction with dynamic optimising of the ion mobility separation conditions for particular target ions.

The ion mobility separation device according to the preferred embodiment may be located upstream and/or downstream of one or more mass analysers and/or one or more fragmentation or activation devices.

Although the present invention has been described with reference to preferred embodiments, it will be understood by those skilled in the art that various changes in form and detail may be made without departing from the scope of the invention as set forth in the accompanying claims.

The invention claimed is:

1. Apparatus arranged and adapted to separate ions temporally according to their ion mobility or differential ion mobility comprising:
   an ion guide comprising a plurality of electrodes; and
   a first device arranged and adapted to remove undesired ions remaining within said ion guide after ions of interest have exited said ion guide;
   wherein said apparatus comprises a control system which is arranged and adapted:
   (i) to cause said apparatus to operate in a first mode of operation wherein a first plurality of ions are separated temporally according to their ion mobility or differential ion mobility during a first time period T1, wherein the first plurality of ions comprises ions of interest and other ions, the other ions being undesired ions, wherein the ions of interest of the first plurality of ions exit the ion guide within said first time period T1, and the undesired ions of the first plurality of ions remain in the ion guide after the first time period T1; and then
   (ii) to switch said apparatus to operate in a second mode of operation wherein the undesired ions of the first plurality of ions that remain in the ion guide after the first time period T1 are rapidly flushed out from said ion guide during a second time period T2;
   wherein said control system is further arranged and adapted to during said first mode of operation apply either:
   a) one or more first transient DC voltages to said electrodes having a first amplitude and/or a first transient velocity: or
   b) one or more first DC voltages to said electrodes so as to produce a first potential gradient within or along said ion guide;
   so as to cause the first plurality of ions to separate temporally within said ion guide according to their ion mobility or differential ion mobility during said first mode of operation; and
   wherein said control system is further arranged and adapted to during said second mode of operation apply either:
   a) one or more second transient DC voltages to said electrodes having a second amplitude and/or a second transient velocity: or
   b) one or more second DC voltages to said electrodes so as to produce a second potential gradient within or along said ion guide;
   so as to cause the undesired ions of the first plurality of ions to be ejected from said ion guide during said second mode of operation.

2. Apparatus as claimed in claim 1, further comprising a second device which is arranged and adapted to pulse ions into said ion guide, wherein said second device comprises an ion trap or ion gate, and wherein said second device is arranged and adapted to pulse a first group of ions into said ion guide and said first device is arranged and adapted to remove said undesired ions from said ion guide prior to the introduction of a second or subsequent pulse of ions into said ion guide.

3. Apparatus as claimed in claim 1, wherein said control system is arranged and adapted to set said first time period T1 and said second time period T2 so that T2<T1, wherein said control system is arranged and adapted to repeatedly switch between at least said first mode of operation and said second mode of operation multiple times during the course of a single acquisition.

4. Apparatus as claimed in claim 1, wherein said control system is arranged and adapted to perform at least one of:
   progressively vary, decrease or increase said first time period T1 during the course of an acquisition; and
   progressively vary, decrease or increase said second time period T2 during the course of an acquisition, or maintain said second time period T2 substantially constant during the course of an acquisition.

5. Apparatus as claimed in claim 1, wherein said first amplitude is selected from the group consisting of: (i)<5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V, wherein said second amplitude is selected from the group consisting of: (i)<5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V, and wherein said second amplitude is greater than said first amplitude.

6. Apparatus as claimed in claim 1, wherein said control system is arranged and adapted to maintain said first amplitude constant during said first mode of operation.

7. Apparatus as claimed in claim 1, wherein said one or more first transient DC voltages or potentials are applied to said electrodes at a first rate or first velocity during said first mode of operation so as to cause ions to separate temporally within said ion guide according to their ion mobility or differential ion mobility during said first mode of operation, wherein said first rate or first velocity is selected from the group consisting of: (i)<50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s, wherein said control system is arranged and adapted to maintain said first rate or first velocity substantially constant during said first mode of operation, or wherein said control system is arranged and adapted to vary, increase or decrease said first rate or first velocity during said first mode of operation.

8. Apparatus as claimed in claim 1, wherein in said first mode of operation said ion guide is maintained at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar, and wherein in said second mode of operation said ion guide is maintained at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

9. Apparatus as claimed in claim 1, wherein the magnitude of said second potential gradient is greater than the magnitude of said first potential gradient.

10. Apparatus as claimed in claim 1, wherein said one or more second transient DC voltages or potentials are applied to said electrodes at a second rate or second velocity during said second mode of operation so as to cause ions to be ejected from said ion guide during said second mode of operation, wherein said second rate or second velocity is selected from the group consisting of: (i)<50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s, and wherein said second rate or second velocity is less than said first rate or first velocity.

11. Apparatus as claimed in claim 1, wherein said control system is arranged and adapted to vary, decrease, or increase said first amplitude during said first mode of operation.

12. A method of separating ions temporally according to their ion mobility or differential ion mobility comprising:
providing an ion guide comprising a plurality of electrodes; and
removing undesired ions remaining within said ion guide after ions of interest have exited said ion guide;
said method further comprising:
during a first mode of operation either:
a) applying one or more first transient DC voltages to said electrodes having a first amplitude and/or a first transient velocity; or
b) applying one or more first DC voltages to said electrodes so as to produce a first potential gradient within or along said ion guide;
so as to cause ions of a first plurality of ions to separate temporally within said ion guide according to their ion mobility or differential ion mobility during a first time period T1 in said first mode of operation, wherein the first plurality of ions comprises ions of interest and other ions, the other ions being undesired ions, wherein the ions of interest of the first plurality of ions exit the ion guide within said first time period T1, and the undesired ions of the first plurality of ions remain in the ion guide after the first time period T1; and then
during a second mode of operation either:
a) applying one or more second transient DC voltages to said electrodes having a second amplitude and/or a second transient velocity; or
b) applying one or more second DC voltages to said electrodes so as to produce a second potential gradient within or along said ion guide during said second mode of operation;
so as to cause the undesired ions that remain in the ion guide after the first time period T1 to be rapidly flushed out from said ion guide during a second time period T2 in said second mode of operation.

13. A method as claimed in claim 12, further comprising pulsing ions into said ion guide, comprising using an ion trap or ion gate to pulse ions into said ion guide, and comprising pulsing a first group of ions into said ion guide and removing undesired ions from said ion guide prior to the introduction of a second or subsequent pulse of ions into said ion guide.

14. A method as claimed in claim 12, further comprising setting said first time period T1 and said second time period T2 so that T2<T1, comprising repeatedly switching between at least said first mode of operation and said second mode of operation multiple times during the course of a single acquisition, and further comprising at least one of:
progressively varying, decreasing or increasing said first time period T1 during the course of an acquisition; and
progressively varying, decreasing or increasing said second time period T2 during the course of an acquisition, or maintaining said second time period T2 substantially constant during the course of an acquisition.

15. A method as claimed in claim 12, wherein said first amplitude is selected from the group consisting of: (i)<5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V,
wherein said second amplitude is selected from the group consisting of: (i)<5V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; and (xi) >50 V,
wherein said second amplitude is greater than said first amplitude.

16. A method as claimed in claim 12, further comprising applying said one or more first transient DC voltages or potentials to said electrodes at a first rate or first velocity during said first mode of operation so as to cause ions to separate temporally within said ion guide according to their ion mobility or differential ion mobility during said first mode of operation, wherein said first rate or first velocity is selected from the group consisting of: (i)<50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s, and further comprising:
maintaining said first rate or first velocity substantially constant during said first mode of operation; or
varying, increasing or decreasing said first rate or first velocity during said first mode of operation.

17. A method as claimed in claim 12, further comprising maintaining in said first mode of operation said ion guide at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar, and further comprising maintaining in said second mode of operation said ion guide at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

18. A method as claimed in claim 12, wherein said second DC voltage or potential gradient is of greater magnitude than said first DC voltage or potential gradient, wherein said one or more second transient DC voltages or potentials are applied to said electrodes at a second rate or second velocity during said second mode of operation so as to cause ions to be ejected from said ion guide during said second mode of operation, wherein said second rate or second velocity is selected from the group consisting of: (i)<50 m/s; (ii) 50-100 m/s; (iii) 100-150 m/s; (iv) 150-200 m/s; (v) 200-250 m/s; (vi) 250-300 m/s; (vii) 300-350 m/s; (viii) 350-400 m/s; (ix) 400-450 m/s; (x) 450-500 m/s; (xi) 500-550 m/s; (xii) 550-600 m/s; (xiii) 600-650 m/s; (xiv) 650-700 m/s; (xv) 700-750 m/s; (xvi) 750-800 m/s; (xvii) 800-850 m/s; (xviii) 850-900 m/s; (xix) 900-950 m/s; (xx) 950-1000 m/s; and (xxi) >1000 m/s, and wherein said second rate or second velocity is less than said first rate or first velocity.

19. A method as claimed in claim 12, further comprising maintaining said first amplitude constant during said first mode of operation.

20. A method as claimed in claim 12, further varying, decreasing, or increasing said first amplitude during said first mode of operation.

* * * * *